United States Patent [19]
Gudaitis

[11] Patent Number: 5,392,784
[45] Date of Patent: Feb. 28, 1995

[54] VIRTUAL RIGHT LEG DRIVE AND AUGMENTED RIGHT LEG DRIVE CIRCUITS FOR COMMON MODE VOLTAGE REDUCTION IN ECG AND EEG MEASUREMENTS

[75] Inventor: Algird M. Gudaitis, Stowe, Mass.

[73] Assignee: Hewlett-Packard Company, Palo Alto, Calif.

[21] Appl. No.: 109,880

[22] Filed: Aug. 20, 1993

[51] Int. Cl.[6] .......................................... A61B 5/0428
[52] U.S. Cl. ...................................... 128/696; 128/902
[58] Field of Search ................................ 128/696, 902

[56] References Cited

U.S. PATENT DOCUMENTS

| | | | |
|---|---|---|---|
| 3,476,103 | 11/1969 | Stenger et al. | 128/696 |
| 3,498,288 | 3/1970 | Max et al. | 128/696 |
| 3,757,778 | 9/1973 | Graham | 128/696 |
| 4,191,195 | 3/1980 | Miller | 128/696 |
| 4,494,551 | 1/1985 | Little, III et al. | 128/696 |
| 4,890,630 | 1/1990 | Kroll et al. | 128/696 |
| 4,981,141 | 1/1991 | Segalowitz | 128/696 |
| 5,002,063 | 3/1991 | Haner | 128/696 |
| 5,020,541 | 6/1991 | Marriott | 128/696 |
| 5,022,404 | 6/1991 | Hafner | 128/696 |

OTHER PUBLICATIONS

Winter et al, "Reduction of Interference Due to Common Mode Voltage in Biopotential Amplifiers", IEEE Trans. BioMed. Engr., vol. BME-30, No. 1, Jan. 1983 pp, 58-61.

Winter et al, "Driven-Right-Leg Circuit Design", IEEE Trans. Biomedical Engr., vol. BME-30, No. 1, Jan. 1983., pp. 62-66.

*Primary Examiner*—William E. Kamm

[57] ABSTRACT

An isolated amplifier, typically a biomedical amplifier, includes a main amplifier having inputs for receiving signals, a circuit for sensing a common mode voltage received by the inputs from the electrodes and providing a compensation voltage representative of the common mode voltage, and a capacitance to chassis ground for receiving a voltage representative of the compensation voltage. The circuit and the capacitance cause the amplifier power supply voltages to track the common mode voltage. The capacitance permits the feedback loop gain to be increased, thereby reducing common mode voltage errors.

20 Claims, 5 Drawing Sheets

VIRTUAL RIGHT LEG DRIVE AND AUGMENTED RIGHT LEG DRIVE CIRCUITS FOR COMMON MODE VOLTAGE REDUCTION IN ECG AND EEG MEASUREMENTS

FIELD OF THE INVENTION

This invention relates to amplifiers that are isolated from earth ground and, more particularly, to biomedical amplifier circuits having high common mode voltage attenuation.

BACKGROUND OF THE INVENTION

Biomedical measurements, such as electrocardiogram (ECG) and electroencephalogram (EEG) measurements, are typically made by affixing two or more electrodes to a patient. The electrodes are electrically connected to an instrumentation amplifier which measures the electrical potential between the electrodes. One source of measurement error is the common mode voltage applied to the amplifier. The common mode voltage is induced on the patient by nearby power conductors, static charge and other electrical sources. The common mode voltage is applied equally to both amplifier inputs and, for an ideal amplifier, has no effect on the amplifier output. While practical amplifiers attenuate common mode voltages by 60 dB or more, an output voltage is produced, thereby introducing a measurement error.

One prior art approach to reducing the errors that result from common mode voltage is to connect the patient to earth ground. This approach has been discontinued for safety reasons. Reduction of common mode voltage errors in biopotential amplifiers is discussed by B. B. Winter et al in "Reduction Of Interference Due to Common Mode Voltage in Biopotential Amplifiers", *IEEE Transactions on Biomedical Engineering*, Vol. BME-30, No. 1, January 1983, pages 58–62.

Another prior art approach, often called a "right leg drive circuit", is exemplified by the circuit shown in FIG. 1. Electrodes 10 and 12, represented in FIG. 1 as resistors, are attached to a patient 14. The electrodes 10 and 12 are connected to inputs 16 and 18, respectively, of a differential amplifier 20 (including operational amplifiers 25 and 26, and resistors 27, 28 and 29). A common mode voltage applied to the inputs of amplifier 20 is sensed by resistors 22 and 24 connected between the outputs of amplifier 20. A sensed voltage representative of the common mode voltage is applied to the input of an integrating amplifier 30. The output of amplifier 30 is connected to a third electrode 32 attached to patient 14. Typically, the third electrode 32 is connected to the patient's right leg for ECG and to the reference electrode for EEG. The integrating amplifier 30 completes a feedback loop which supplies current to the patient 14 to reduce the common mode input voltage change relative to the power supply voltages for amplifier 20. Further details regarding the right leg drive circuit are described by B. B. Winter et al in "Driven-Right-Leg Circuit Design", *IEEE Transactions on Biomedical Engineering*, Vol. BME-30, No. 1, January 1983, pages 62–66. The major limitations of the right leg drive circuit are that a third connection to the patient is required and that the 60 Hz common mode voltage attenuation is typically only about 100 dB.

Yet another prior art circuit is disclosed in U.S. Pat. No. 4,191,195 issued Mar. 4, 1980 to Miller. A voltage representative of the common mode voltage is amplified and is applied to a capacitor connected to circuit ground. The disclosed circuit imprecisely attenuates the common mode signal by imprecisely raising the ground referenced common mode impedance.

Still another prior art circuit is a modification of the right leg drive circuit shown in FIG. 1. A negative capacitance amplifier is connected between earth ground and the inputs to the instrumentation amplifier. The negative capacitance amplifier imprecisely attenuates the common mode signal by imprecisely raising the ground referenced common mode impedance.

SUMMARY OF THE INVENTION

In accordance with the present invention, an isolated amplifier comprises a main amplifier having first and second inputs for receiving signals, the main amplifier receiving one or more power supply voltages and having a circuit ground electrically isolated from chassis ground, means for sensing the common mode voltage received by the first and second inputs and providing a compensation voltage representative of the common mode voltage, and a capacitance to chassis ground for receiving a voltage representative of the compensation voltage. The means for sensing and the capacitance cause the power supply voltages to track the common mode voltage. The isolated amplifier is typically a biomedical amplifier and receives signals from first and second electrodes affixed to a patient. The means for sensing typically includes a compensation amplifier for amplifying the common mode voltage.

In a first embodiment of the invention, the output of the compensation amplifier is coupled to the capacitance, and a third patient electrode is not required.

In a second embodiment of the invention, the biomedical amplifier includes means for coupling the output of the compensation amplifier to a third electrode affixed to the patient such that the voltage applied to the third electrode is attenuated relative to a voltage applied to the capacitor. The capacitance serves as an augmentation capacitance in the second embodiment. The coupling means preferably comprises a resistive attenuator connected between the output of the compensation amplifier and the third electrode.

In a third embodiment of the invention, the biomedical amplifier includes means for coupling the output of the compensation amplifier to a third electrode affixed to the patient and further includes means for coupling an amplified version of the compensation amplifier output to the capacitance. The capacitance serves as an augmentation capacitance in the third embodiment. The coupling means preferably comprises an additional amplifier connected between the output of the compensation amplifier and the capacitance.

The patient electrodes, the main amplifier, the compensation amplifier and the capacitance form a feedback loop. The capacitance to chassis ground has a value selected to introduce a zero in the frequency response of the feedback loop at a frequency lower than the unity gain frequency of the feedback loop. This permits the gain of the feedback loop to be increased, thereby reducing the error resulting from common mode voltage.

According to another aspect of the invention, a double shielded cable is connected between the electrodes and the main amplifier. The double shielded cable includes an outer shield, an inner shield and one or more signal conductors. The capacitance between the outer shield of the double shielded cable and chassis ground serves as the capacitance which is used to reduce common mode voltages errors.

BRIEF DESCRIPTION OF THE DRAWINGS

For a better understanding of the present invention, reference is made to the accompanying drawings, which are incorporated herein by reference and in which.

DETAILED DESCRIPTION

Figure 2:
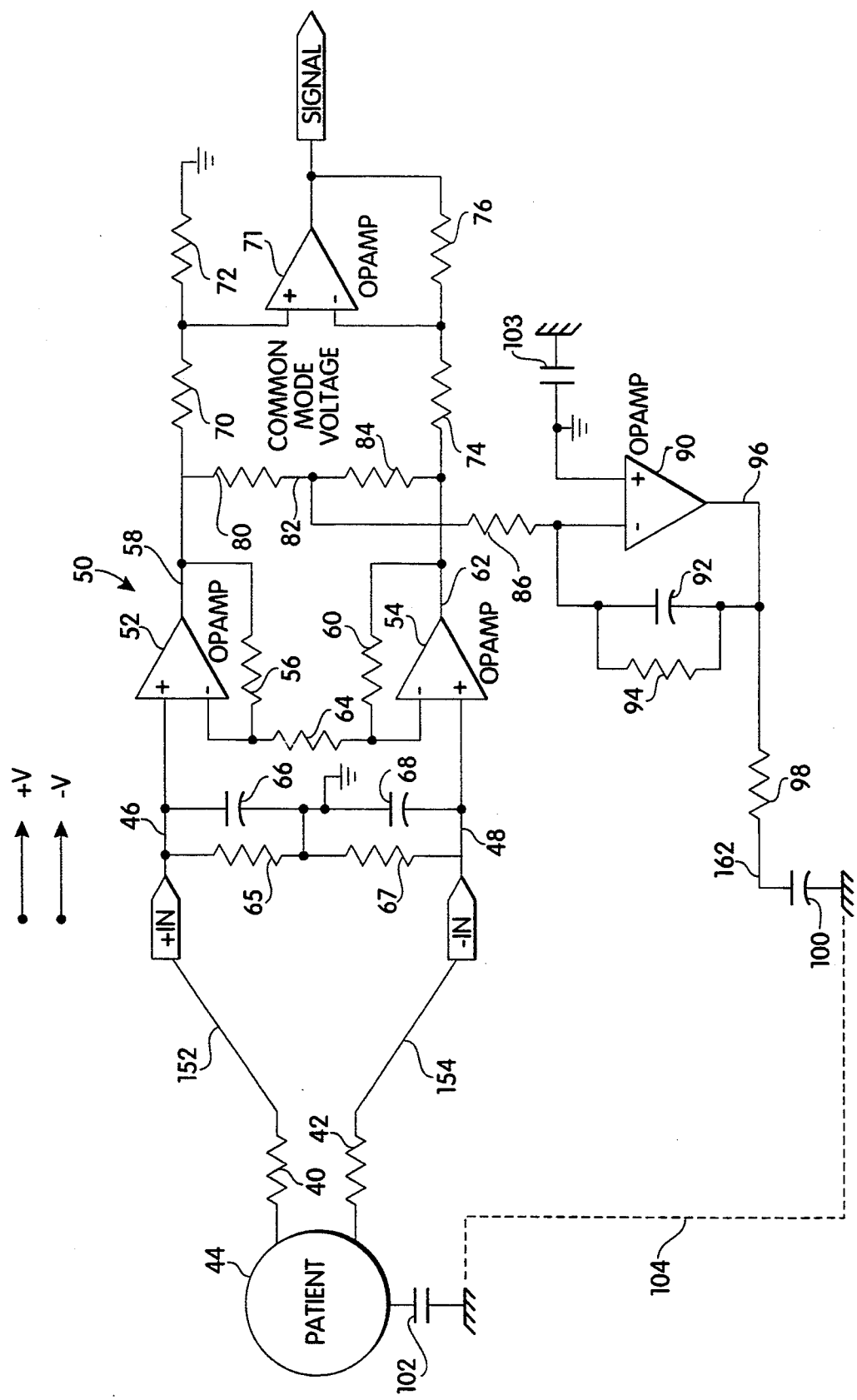
FIG. 2 is a schematic diagram of a virtual right leg drive biomedical amplifier in accordance with the present invention.

A schematic diagram of an isolated amplifier, such as a biomedical amplifier, in accordance with a first embodiment of the invention is shown in FIG. 2. The amplifier is isolated from chassis, or earth, ground. The circuit is called a "virtual right leg drive" circuit because the need for a third electrode, typically connected to the right leg of the patient, is eliminated. Electrodes 40 and 42, represented in FIG. 2 as resistors, are connected to a patient 44. The electrodes may be ECG, EEG or other biopotential sensing electrodes. The electrodes 40 and 42 are connected to inputs 46 and 48, respectively, of a differential amplifier 50, which serves as the main biopotential amplifier. The differential amplifier 50 includes operational amplifiers 52 and 54, and resistors 56, 60 and 64. Inputs 46 and 48 are connected to the noninverting inputs of operational amplifiers 52 and 54, respectively. Feedback resistor 56 is connected between an output 58 and the inverting input of amplifier 52. Feedback resistor 60 is connected between an output 62 and the inverting input of amplifier 54. Resistor 64 is connected between the inverting inputs of amplifiers 52 and 54. A resistor 65 and a capacitor 66 are connected in parallel between input 46 and circuit ground. A resistor 67 and a capacitor 68 are connected in parallel between input 48 and circuit ground. The resistors 65 and 67 provide bias current to the noninverting inputs of operational amplifiers 52 and 54, respectively.

The outputs 58 and 62 of amplifiers 52 and 54, respectively, are connected to a differential to single-ended converter, including an operational amplifier 71 and resistors 70, 72, 74 and 76. It will be understood that this circuit is only one example of a suitable differential to single-ended converter. In another embodiment, the outputs 58 and 62 of amplifiers 52 and 54 are supplied to an analog-to-digital converter which converts the amplifier outputs to digital samples and subtracts the digital values. It will also be understood that the differential amplifier 50 shown in FIG. 2 is shown by way of example and that other amplifier circuits are included within the scope of the present invention. In another embodiment, the functions of amplifiers 52, 54 and 71 are combined in a single integrated circuit. This integrated circuit is commercially available from Analog Devices, Inc. as type AD620. Furthermore, the isolated amplifier of the present invention can receive input signals from sources other than electrodes 40 and 42.

Referring again to FIG. 2, a resistor 80 is connected between output 58 of amplifier 52 and a node 82. A resistor 84 is connected between output 62 of amplifier 54 and node 82. The voltage at node 82 is representative of the common mode voltage applied to inputs 46 and 48 from patient 44. A resistor 86 is connected between node 82 and the inverting input of an operational amplifier 90. A capacitor 92 and a resistor 94 are connected in parallel between an output 96 and the inverting input of operational amplifier 90. The noninverting input of operational amplifier 90 is connected to circuit ground. A resistor 98 and a capacitor 100 are connected in series between the output 96 of operational amplifier 90 and chassis ground. Stray capacitance between the patient 44 and chassis ground is represented by a capacitance 102. Stray capacitance between the amplifier circuit and chassis ground is represented by a capacitor 103. The amplifiers 52, 54, 71 and 90 receive power supply voltages $+V$ and $-V$ from power supplies (not shown), which are isolated from chassis ground.

Figure 1:
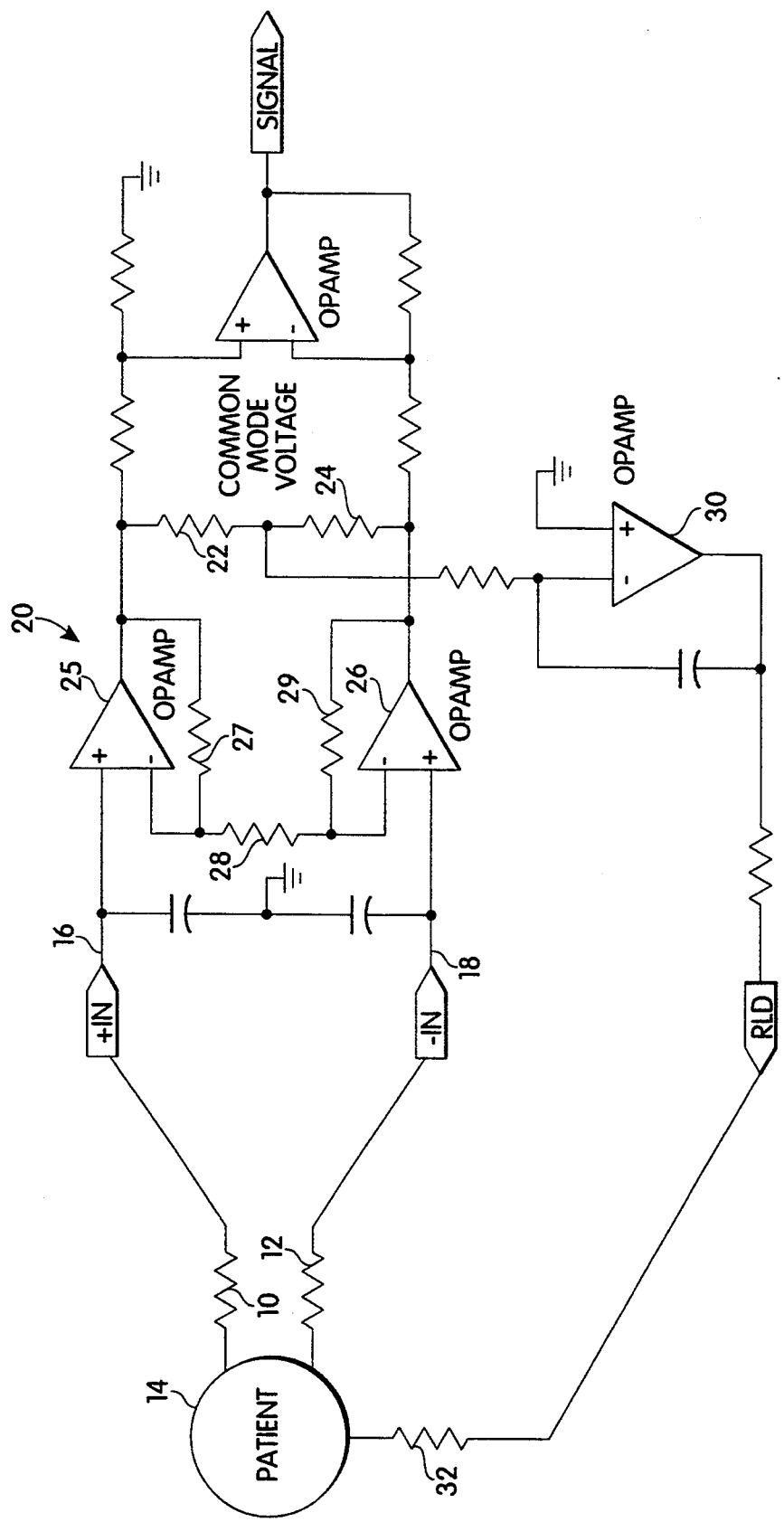
FIG. 1 is a schematic diagram of a right leg drive circuit in accordance with the prior art.

In the circuit of FIG. 2, the operational amplifier 90, capacitor 100 and related components reduce the effect of common mode voltage input from patient 44 without requiring a third electrode attached to the patient. The DC feedback path that exists in the circuit of FIG. 1 is broken in the circuit of FIG. 2. The capacitor 100, chassis ground and stray capacitance 102 provide a high frequency feedback path, indicated by dashed line 104 in the circuit of FIG. 2. A common mode voltage compensation circuit including operational amplifier 90, capacitor 100 and related components, in effect, causes the power supply voltages $+V$ and $-V$ to track the voltage of patient 44. The current to perform this tracking is obtained through capacitor 100. The resistor 94 limits the DC gain of operational amplifier 90 and prevents operational amplifier 90 from saturating.

The capacitor 100 preferably has a high voltage rating, typically several hundred to several thousand volts, since any voltage on the patient 44 relative to chassis ground is applied to it. To meet patient safety requirements, the value of capacitor 100 is limited to about 200 picofarads. Typically, the value of capacitor 100 is in a range of about 10 to 200 picofarads. A further requirement of the circuit of FIG. 2 is that the operational amplifier 90 must accommodate voltage swings somewhat greater than the voltage swings that may be expected on the patient. The circuit shown in FIG. 2 has improved performance at high frequencies as compared with the circuit of FIG. 1 because of increased gain at low and middle range frequencies without loop stability problems, thereby providing increased common mode voltage attenuation.

The compensation amplifier is illustrated in FIG. 2 as an integrator including operational amplifier 90, capacitor 92 and resistor 86. In general, the compensation amplifier is required to have high gain at low frequencies, a controlled decrease in gain with increasing frequency and a reduction to unity gain by the crossover frequency of the feedback loop. While the compensation amplifier is typically implemented as an integrator, other circuits meeting these requirements can be utilized.

Figure 3:
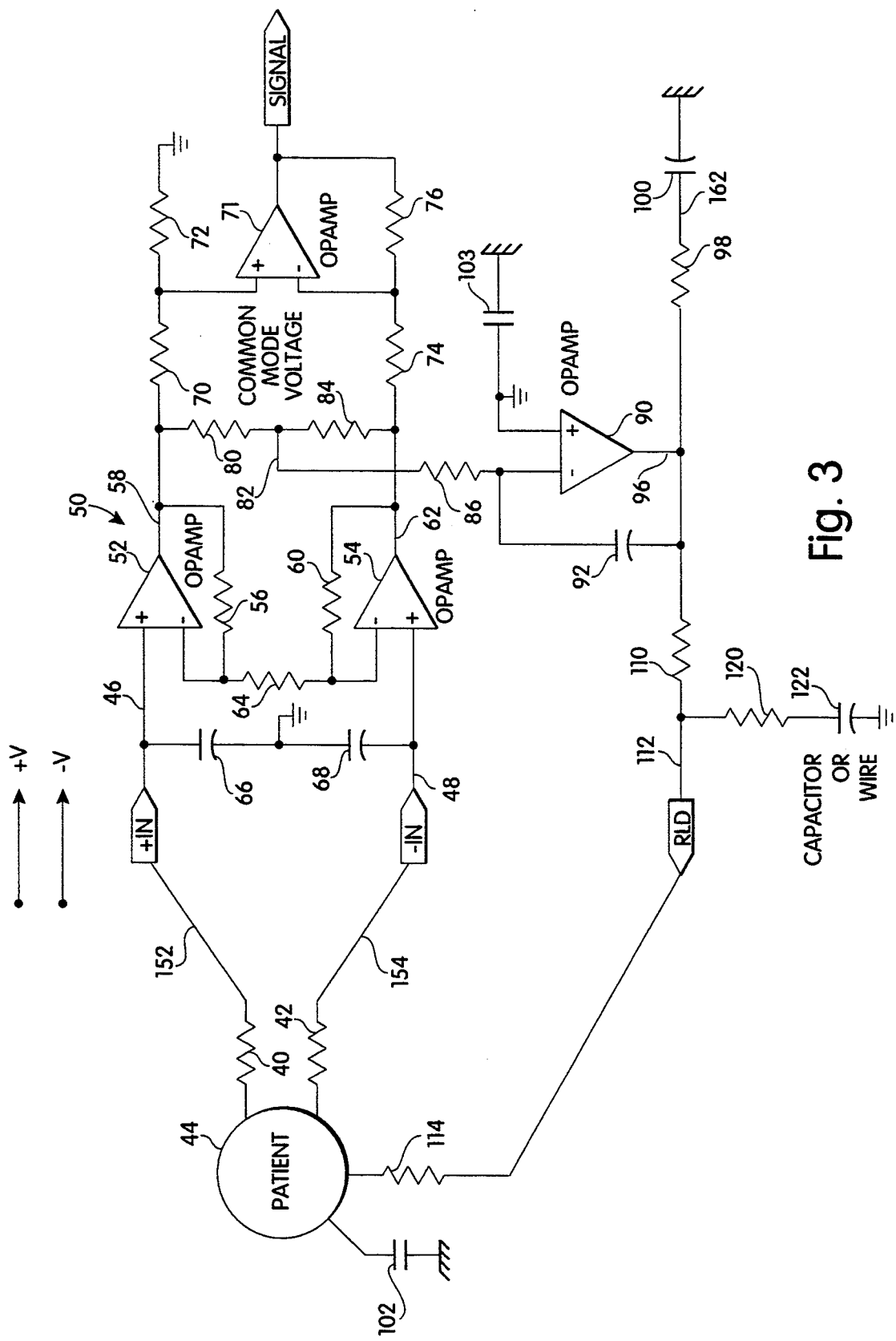
FIG. 3 is a schematic diagram of an augmented right leg drive biomedical amplifier in accordance with the present invention.

A schematic diagram of a biomedical amplifier in accordance with a second embodiment of the invention is shown in FIG. 3. Like elements in FIGS. 2 and 3 have the same reference numerals. The circuit of FIG. 3 is called an "augmented right leg drive" circuit. The output 96 of operational amplifier 90 is coupled through resistor 98 and capacitor 100 to chassis ground as in FIG. 2. The output 96 of operational amplifier 90 is also connected through a resistor 110 to a node 112. The node 112 is connected to a third electrode 114 affixed to patient 44 and is also connected through a resistor 120 and an optional capacitor 122 to circuit ground. The resistors 110 and 120 form a resistive attenuator such that the voltage at node 112 is reduced as compared with the voltage at output 96 of operational amplifier 90. The voltage at node 112 is typically reduced by a factor of about 10 to 20, but can be reduced by other factors within the scope of the invention. The capacitor 122 reduces the attenuation at low frequencies, when used. When the capacitor 122 is not used, the resistor 120 is connected directly to circuit ground.

The circuit path from output 96 of operational amplifier 90 through resistor 110 and third electrode 114 to patient 44 is a feedback path similar to that used in the circuit of FIG. 1. This feedback path is augmented by an AC feedback path from output 96 through resistor 98, capacitor 100, chassis ground, and stray capacitance 102 to patient 44. In this embodiment, capacitor 100 serves as an augmentation capacitor. The attenuation provided by resistors 110 and 120 ensures that the AC feedback path through resistor 98, capacitor 100, chassis ground and capacitance 102 dominates over the feedback path through resistor 110 and electrode 114 at frequencies near the unity gain frequency of the feedback loop. Because of patient safety requirements, capacitor 100 cannot be increased in size until the AC feedback path dominates over the direct path through resistor 110 to patient 44. As noted above, the value of capacitor 100 is limited to about 200 picofarads. However, capacitor 100 can be made large enough to dominate over an attenuated feedback signal through resistor 110, shunted by resistor 120, to patient 44. The configuration of FIG. 3 has the effect of adding a zero in the feedback loop response, which reduces the phase shift around the loop, thereby allowing an increase in the unity gain crossover frequency and permitting the gain to be increased at lower frequencies, as compared with the prior art circuit shown in FIG. 1. By increasing the loop gain, the common mode voltage attenuation is increased.

Representative values for one example of the circuit shown in FIG. 3 are given in Table I below. It will be understood that these values are in no way limiting and that other combinations of values can be utilized within the scope of the present invention. Furthermore, the invention is not limited to the circuit configurations shown in FIGS. 2 to 4.

TABLE I

| Component | Value |
|---|---|
| Capacitors 66 and 68 | 740 picofarads |
| Amplifiers 52 and 54 | OP27 |
| Resistors 56 and 60 | 10K ohms |
| Resistor 64 | 1K ohms |
| Resistors 80 and 84 | 6K ohms |
| Resistor 86 | 0 |
| Amplifier 90 | LT1057 |
| Capacitor 92 | 15 picofarads |
| Resistor 98 | 1K ohms |
| Capacitor 100 | 80 picofarads |
| Resistor 110 | 470K ohms |
| Resistor 120 | 22K ohms |

TABLE I-continued

| Component | Value |
|---|---|
| Capacitor 122 | 0.22 microfarad |

Note 1 - The values for capacitors 66 and 68 include the capacitance of the cable which connects the electrodes to the amplifier.
Note 2 - The value of resistor 86 is zero in this example because the parallel combination of resistors 80 and 84 function as an input resistor to amplifier 90.

Figure 4:
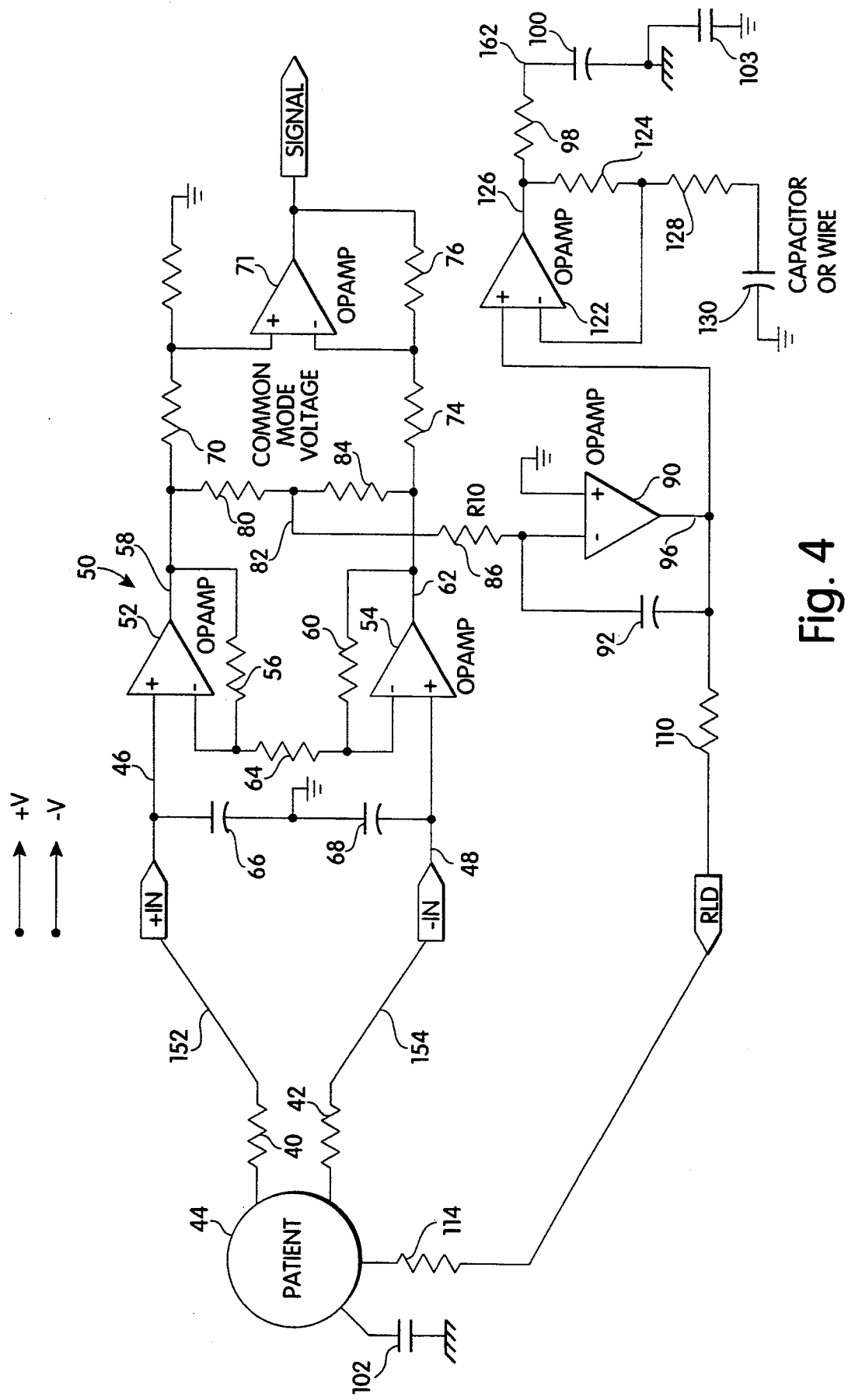
FIG. 4 is a schematic diagram of an alternate augmented right leg drive biomedical amplifier in accordance with the present invention.

A schematic diagram of a biomedical amplifier in accordance with a third embodiment of the invention is shown in FIG. 4. Like elements in FIGS. 2 and 4 have the same reference numerals. The circuit of FIG. 4 is an alternate to the "augmented right leg drive" circuit of FIG. 3. The output 96 of operational amplifier 90 is connected through a resistor 110 to the third electrode 114 affixed to patient 44. The output 96 of an operational amplifier 90 is also connected to the noninverting input of an operational amplifier 122. A feedback resistor 124 is connected between an output 126 and the inverting input of operational amplifier 122. The inverting input is connected through a resistor 128 and an optional capacitor 130 to circuit ground. When the capacitor 130 is not used, the resistor 128 is connected directly to circuit ground. The output 126 of operational amplifier 122 is connected through resistor 98 and capacitor 100 to chassis ground. The capacitor 100 in this embodiment also serves as an augmentation capacitor. Typically, capacitor 92 in FIG. 4 is 10 to 20 times the value of capacitor 92 in FIG. 3 to compensate for the gain of the operational amplifier 122 circuit.

The output 96 of operational amplifier 90 is supplied to third electrode 114 without attenuation and is amplified by operational amplifier 122 for application to capacitor 100. Typically, the gain of operational amplifier 122 is on the order of about 10 to 20, but the operational amplifier 122 can have other gain values within the scope of the invention. It can be seen that the circuits of FIGS. 3 and 4 are equivalent in the sense that the voltage applied to third electrode 114 is smaller than the voltage applied to capacitor 100. In the circuit of FIG. 3 the voltage ratio is achieved by attenuation of the voltage applied to third electrode 114. In the circuit of FIG. 4, the voltage ratio is achieved by amplification of the voltage applied to capacitor 100. Operation of the circuit of FIG. 4 is essentially the same as the operation of the circuit of FIG. 3.

Figure 5:
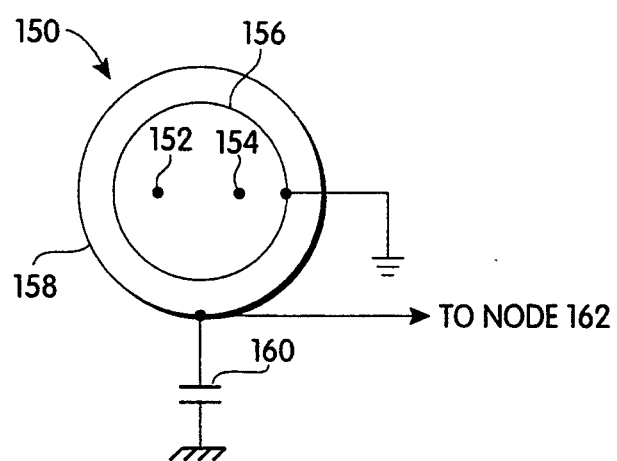
FIG. 5 is a schematic cross-sectional representation of a double shielded cable in accordance with a feature of the present invention.

A further feature of the invention is illustrated with reference to FIG. 5, which shows a schematic cross-section of a double shielded cable 150. Double shielded cable 150 includes signal conductors 152 and 154 which are used for interconnection of electrodes 40 and 42 to inputs 46 and 48, respectively, of differential amplifier 50. An inner shield 156 is connected to circuit ground. An outer shield 158 has a stray capacitance 160 to chassis ground. In accordance with this feature of the invention, the stray capacitance 160 is used as the capacitor 100 in FIGS. 2, 3 and 4. When the stray capacitance 160 is used in this manner, the outer shield 158 of the cable 150 is connected to node 162 in FIGS. 2, 3 and 4, and the respective discrete capacitors are not required. This eliminates the requirement for the discrete high voltage capacitor 100.

While there have been shown and described what are at present considered the preferred embodiments of the present invention, it will be obvious to those skilled in the art that various changes and modifications may be made therein without departing from the scope of the invention as defined by the appended claims.

What is claimed is:

1. An isolated amplifier for use in a system having an earth ground comprising:
    a main amplifier having first and second inputs for receiving signals, said main amplifier including means for receiving at least one power supply voltage and having a circuit ground electrically isolated from said earth ground;
    means for sensing a common mode voltage received by said first and second inputs and having an output for providing a compensation voltage representative of said common mode voltage; and
    a capacitance to said earth ground for receiving said compensation voltage, said means for sensing and said capacitance causing said at least one power supply voltage to track said common mode voltage.

2. An isolated amplifier as defined in claim 1 wherein said means for sensing includes a compensation amplifier for amplifying said common mode voltage.

3. An isolated amplifier as defined in claim 2 wherein said compensation amplifier comprises an integrator, and further including means for limiting the DC gain of said integrator to prevent saturation thereof.

4. An isolated amplifier as defined in claim 2 wherein said main amplifier and said compensation amplifier comprise elements in a feedback loop having a unity gain frequency and wherein said capacitance has a value selected to introduce a zero in the frequency response of said feedback loop at a frequency lower than said unity gain frequency.

5. An isolated amplifier as defined in claim 1 further including a bias resistor connected between each of the first and second inputs of said main amplifier and said circuit ground.

6. An isolated amplifier as defined in claim 1 wherein said capacitance comprises an augmentation capacitance and further including means responsive to the compensation voltage provided by said means for sensing for coupling a first voltage representative of said compensation voltage to a patient and for coupling a second voltage representative of said compensation voltage to said augmentation capacitance, said first voltage being attenuated relative to said second voltage by said means for coupling.

7. An isolated amplifier as defined in claim 6 wherein said means for coupling comprises a resistive attenuator coupled to the output of said means for sensing.

8. An isolated amplifier as defined in claim 1 wherein said capacitance comprises an augmentation capacitance and further including means responsive to the compensation voltage provided by said means for sensing for coupling a first voltage representative of said compensation voltage to a patient and for coupling a second voltage representative of said compensation voltage to said augmentation capacitance, said second voltage being amplified relative to said first voltage by said means for coupling.

9. An isolated amplifier as defined in claim 8 wherein said means for coupling comprises an additional amplifier connected between the output of said means for sensing and said augmentation capacitance.

10. An isolated amplifier as defined in claim 1 further including a double shielded cable connected to said main amplifier, said double shielded cable comprising an outer shield connected to receive a voltage representative of said compensation voltage, an inner shield connected to said circuit ground and signal conductors connected to the first and second inputs of said main amplifier, said capacitance comprising a stray capacitance between the outer shield of said double shielded cable and said earth ground.

11. An isolated amplifier as defined in claim 1 wherein said main amplifier comprises a differential amplifier.

12. An isolated amplifier for use in a system having an earth ground comprising:
    a main amplifier having first and second inputs for receiving signals, said main amplifier having a circuit ground electrically isolated from said earth ground;
    a circuit for sensing a common mode voltage received by said first and second inputs and having an output for providing a compensation voltage representative of said common mode voltage;
    an augmentation capacitance connected to said earth ground;
    means responsive to the compensation voltage provided by said circuit for coupling a first voltage representative of said compensation voltage to a patient and for coupling a second voltage representative of said compensation voltage to said capacitance, said second voltage being larger than said first voltage.

13. An isolated amplifier as defined in claim 12 wherein said means for coupling comprises a resistive attenuator coupled to the output of said circuit.

14. An isolated amplifier as defined in claim 12 wherein said means for coupling comprises an additional amplifier connected between the output of said circuit and said augmentation capacitance.

15. An isolated amplifier as defined in claim 12 further including a double shielded cable connected to said main amplifier, said double shielded cable comprising an outer shield connected to receive a voltage representative of said compensation voltage, an inner shield connected to said circuit ground and signal conductors connected to the first and second inputs of said main amplifier, said augmentation capacitance comprising a stray capacitance between the outer shield of said double shielded cable and said earth ground.

16. An isolated amplifier as defined in claim 12 wherein said augmentation capacitance has a value in a range of about 10-200 picofarads.

17. An isolated amplifier as defined in claim 12 wherein said main amplifier and said circuit comprise elements in a feedback loop having a unity gain frequency and wherein said augmentation capacitance has a value selected to introduce a zero in the frequency response of said feedback loop at a frequency lower than said unity gain frequency.

18. A biomedical amplifier for use in a system having an earth ground comprising:
    a main amplifier having first and second inputs for receiving signals, said main amplifier including means for receiving at least one power supply voltage and having a circuit ground electrically isolated from said earth ground;
    means for sensing a common mode voltage received by said first and second inputs and providing a compensation voltage representative of said common mode voltage; and
    a capacitance to said earth ground for receiving said compensation voltage, said means for sensing and said capacitance causing said at least one power supply voltage to track said common mode voltage.

19. A biomedical amplifier as defined in claim 18 wherein said capacitance comprises an augmentation capacitance and further including means responsive to the compensation voltage provided by said means for sensing for coupling a first voltage representative of said compensation voltage to a patient and for coupling a second voltage representative of said compensation voltage to said augmentation capacitance, said first voltage being attenuated relative to said second voltage by said means for coupling.

20. A biomedical amplifier as defined in claim 18 wherein said capacitance comprises an augmentation capacitance and further including means responsive to the compensation voltage provided by said means for sensing for coupling a first voltage representative of said compensation voltage to a patient and for coupling a second voltage representative of said compensation voltage to said augmentation capacitance, said second voltage being amplified relative to said first voltage by said means for coupling.

* * * * *